(12) United States Patent
Solem et al.

(10) Patent No.: US 7,090,695 B2
(45) Date of Patent: Aug. 15, 2006

(54) METHOD FOR TREATMENT OF MITRAL INSUFFICIENCY

(75) Inventors: Jan O Solem, Stetten (CH); Per O Kimblad, Lund (SE)

(73) Assignee: Edwards Lifesciences AG, (CH)

( * ) Notice: Subject to any disclaimer, the term of this patent is extended or adjusted under 35 U.S.C. 154(b) by 227 days.

(21) Appl. No.: 10/303,765

(22) Filed: Nov. 26, 2002

(65) Prior Publication Data

US 2003/0069636 A1    Apr. 10, 2003

Related U.S. Application Data

(60) Division of application No. 09/775,677, filed on Feb. 5, 2001, which is a continuation-in-part of application No. 09/345,475, filed on Jun. 30, 1999, now Pat. No. 6,210,432.

(51) Int. Cl.
*A61F 2/24* (2006.01)
*A61F 2/06* (2006.01)

(52) U.S. Cl. ............... 623/2.37; 623/2.36; 623/1.15; 623/1.18; 623/1.2; 128/898; 600/37

(58) Field of Classification Search ............ 623/2.36, 623/2.37, 1.1, 1.15, 1.16, 1.18, 1.2, 1.3, 1.31, 623/11.11, 23.7; 600/16–18, 37; 606/191–192, 606/194–195, 198, 108; 128/898

See application file for complete search history.

(56) References Cited

U.S. PATENT DOCUMENTS

| 4,164,046 | A | 8/1979 | Cooley |
| 4,655,771 | A | 4/1987 | Wallsten |
| 4,954,126 | A | 9/1990 | Wallsten |
| 5,006,106 | A | 4/1991 | Angelchik |
| 5,061,275 | A | 10/1991 | Wallsten et al. |
| 5,064,435 | A | 11/1991 | Porter |
| 5,163,955 | A | 11/1992 | Love et al. |
| 5,170,802 | A | 12/1992 | Mehra |
| 5,383,892 | A | 1/1995 | Cardon et al. |
| 5,476,471 | A | 12/1995 | Shifrin et al. |
| 5,531,779 | A | * 7/1996 | Dahl et al. .......... 607/119 |
| 5,534,007 | A | 7/1996 | St. Germain et al. |
| 5,571,135 | A | 11/1996 | Fraser et al. |
| 5,584,879 | A | 12/1996 | Reimold et al. |
| 5,607,444 | A | 3/1997 | Lam |
| 5,674,280 | A | 10/1997 | Davidson et al. |
| 5,713,949 | A | 2/1998 | Jayaraman |
| 5,741,274 | A | 4/1998 | Lenker et al. |
| 5,817,126 | A | 10/1998 | Imran |

(Continued)

FOREIGN PATENT DOCUMENTS

DE    196 05 042 A1    1/1998

(Continued)

OTHER PUBLICATIONS

Gary P. Siskin, MD, "Inferior Vena Cava Filters", www.emedicine.com/radio/topic762.htm.*

(Continued)

*Primary Examiner*—David J. Isabella
*Assistant Examiner*—Urmi Chattopadhyay
(74) *Attorney, Agent, or Firm*—David L. Hauser (57) ABSTRACT

A method for treatment of mitral annulus dilatation comprises reducing the circumference of the mitral valve annulus. The method further comprises inserting an elongate body into the coronary sinus in the vicinity of the posterior leaflet of the mitral valve, fixing the position of the elongate body relative to the coronary sinus, and changing the shape of the elongate body in order to remodel the mitral valve annulus.

14 Claims, 7 Drawing Sheets

U.S. PATENT DOCUMENTS

| | | | |
|---|---|---|---|
| 5,824,071 A | 10/1998 | Nelson et al. | |
| 5,876,419 A | 3/1999 | Carpenter et al. | |
| 5,911,732 A | 6/1999 | Hojeibane | |
| 5,919,233 A | 7/1999 | Knopf et al. | |
| 5,980,552 A | 11/1999 | Pinchasik et al. | |
| 6,006,122 A * | 12/1999 | Smits | 600/373 |
| 6,027,525 A | 2/2000 | Suh et al. | |
| 6,093,203 A | 7/2000 | Uflacker | |
| 6,183,411 B1 | 2/2001 | Mortier et al. | |
| 6,203,556 B1 | 3/2001 | Evans et al. | |
| 6,210,432 B1 | 4/2001 | Solem et al. | |
| 6,221,103 B1 | 4/2001 | Melvin | |
| 6,248,119 B1 | 6/2001 | Solem | |
| 6,250,308 B1 | 6/2001 | Cox | |
| 6,264,602 B1 | 7/2001 | Mortier et al. | |
| 6,264,691 B1 | 7/2001 | Gabbay | |
| 6,325,826 B1 | 12/2001 | Vardi et al. | |
| 6,343,605 B1 | 2/2002 | Lafontaine | |
| 6,350,277 B1 | 2/2002 | Kocur | |
| 6,402,679 B1 | 6/2002 | Mortier et al. | |
| 6,402,680 B1 | 6/2002 | Mortier et al. | |
| 6,402,781 B1 | 6/2002 | Langberg et al. | |
| 6,409,760 B1 | 6/2002 | Melvin | |
| 6,537,314 B1 | 3/2003 | Langberg et al. | |
| 6,569,198 B1 | 5/2003 | Wilson et al. | |
| 6,626,899 B1 | 9/2003 | Houser et al. | |
| 6,656,221 B1 | 12/2003 | Taylor et al. | |
| 6,669,687 B1 | 12/2003 | Saadat | |
| 6,702,826 B1 | 3/2004 | Liddicoat et al. | |
| 6,706,065 B1 | 3/2004 | Langberg et al. | |
| 6,709,456 B1 | 3/2004 | Langberg et al. | |
| 2001/0044568 A1 | 11/2001 | Langberg et al. | |
| 2002/0016628 A1 | 2/2002 | Langberg et al. | |
| 2002/0019660 A1 | 2/2002 | Gianotti et al. | |
| 2002/0022880 A1 | 2/2002 | Melvin | |
| 2002/0042621 A1 | 4/2002 | Liddicoat et al. | |
| 2002/0087173 A1 | 7/2002 | Alferness et al. | |
| 2002/0103532 A1 | 8/2002 | Langberg et al. | |
| 2002/0103533 A1 | 8/2002 | Langberg et al. | |
| 2002/0111533 A1 | 8/2002 | Melvin | |
| 2002/0124857 A1 | 9/2002 | Schroeppel | |
| 2002/0151961 A1 | 10/2002 | Lashinski et al. | |
| 2002/0183835 A1 | 12/2002 | Taylor et al. | |
| 2002/0183836 A1 | 12/2002 | Liddicoat et al. | |
| 2003/0078654 A1* | 4/2003 | Taylor et al. | 623/2.36 |
| 2003/0083538 A1* | 5/2003 | Adams et al. | 600/16 |
| 2003/0130731 A1* | 7/2003 | Vidlund et al. | 623/2.37 |
| 2004/0102841 A1 | 5/2004 | Langberg et al. | |
| 2004/0133192 A1 | 7/2004 | Houser et al. | |
| 2004/0153146 A1 | 8/2004 | Lashinski et al. | |

FOREIGN PATENT DOCUMENTS

| | | |
|---|---|---|
| DE | 196 11 755 A1 | 2/1998 |
| EP | 0 727 239 A2 | 8/1996 |
| WO | WO 95/16407 | 6/1995 |
| WO | WO 96/40356 | 12/1996 |
| WO | WO 98/18411 | 5/1998 |
| WO | WO 99/44534 | 9/1999 |
| WO | WO 99/53977 | 10/1999 |
| WO | WO 00/18320 | 4/2000 |
| WO | WO 00/41649 | 7/2000 |
| WO | WO 00/44313 A1 | 8/2000 |
| WO | WO 01/00111 A1 | 1/2001 |
| WO | WO 01/50985 A1 | 7/2001 |
| WO | WO 01/54618 A1 | 8/2001 |
| WO | WO 01/85061 A2 | 11/2001 |
| WO | WO 01/89426 A1 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/34118 A2 | 5/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |

OTHER PUBLICATIONS

Laaksovirta et al., *Expansion and bioabsorption of the self-reinforced lactic and glycolic acid copolymer prostatic spiral stent*, PubMed, Excerpt from J Urol Sep. 2001; 166(3):919-22, one sheet.

Liu et al., *Sutural expansion osteogenesis for management of the bony-tissue defect in cleft palate repair: experimental studies in dogs*, PubMed, Excerpt from Plast Reconstr Surg May 2000; 105(6):2012-25; discussion 2026-7, two sheets.

Yoneyama et al., *Super-elastic property of Ti-Ni alloy for use in dentistry*, PubMed, Excerpt from Front Med Biol Eng 2000; 10(2):97-103, one sheet.

Kotian, *Shape memory effect and super elasticity it's dental applications*, PubMed, Excerpt from Indian J Dent Res Apr.-Jun. 2001; 12(2): 101-4, one sheet.

Kuo et al., *The use of nickel-titanium alloy in orthopedic surgery in China*, PubMed, Excerpt from Orthopedics Jan. 1989; 12(1):111-6, one sheet.

Civjan et al., *Potential applications of certain nickel-titanium (nitinol) alloys*, PubMed, Excerpt from J Dent Res Jan.-Feb. 1975;54(1):89-96, one sheet.

Brennan, *Suite of Shape-Memory Polymers*, http://pubs.acs.org/cen/topstory/7906/7906notwl.html, News of the Week Materials, Feb. 5, 2001, vol. 79, No. 6, Cenear 79 6 pp. 5, ISSN 0009-2347, three sheets.

Stikeman, *Total Recall*, Technology Review—Innovation: Total Recall, An MIT Enterprise Technology Review, Jun. 2001, two sheets.

European Patent Office Office action dated Dec. 22, 2003 for Application No. 00 946 661.6-2310.

Written Opinion dated Nov. 8, 2002 for International application No. PCT/EP01/10371.

International Search Report dated Apr. 23, 2002 for International application No. PCT/EP 01/10371.

International Search Report dated Mar. 15, 2000 for National application No. SE 9902455-6, 3 sheets.

International Search Report dated Oct. 9, 2002 for National application No. SE 0200073-5, 5 sheets.

International Search Report dated Jun. 5, 2003 for International application No. PCT/EP 02/14655.

Buchanan et al., Circumferential Suture of the Mitral Annulus for Correction of Mitral Regurgitation in Dogs, Veterinary Surgery, 27: 182-193, 1998.

Buchanan et al., Sammarco CD, Circumferential Suture of the Mitral Annulus for Correction of Mitral Regurgitation in Dogs, PubMed, Excerpt from Vet Surg May-Jun. 1998; 27(3): 182-93, abstract, one sheet.

* cited by examiner

METHOD FOR TREATMENT OF MITRAL INSUFFICIENCY

CROSS REFERENCE TO RELATED APPLICATION

This application is a division of U.S. patent application Ser. No. 09/775,677, filed on Feb. 5, 2001, which in turn is a continuation-in-part of U.S. patent application Ser. No. 09/345,475, filed Jun. 30, 1999, now U.S. Pat. No. 6,210,432.

BACKGROUND OF THE INVENTION

1. Technical Field of the Invention

The present invention generally relates to a device and a method for treatment of mitral insufficiency and, more specifically, for treatment of dilatation of the mitral annulus.

2. Description of the Prior Art

Mitral insufficiency can result from several causes, such as ischemic disease, degenerative disease of the mitral apparatus, rheumatic fever, endocarditis, congenital heart disease and cardiomyopathy. The four major structural components of the mitral valve are the annulus, the two leaflets, the chordae and the papillary muscles. Any one or all of these in different combinations may be injured and create insufficiency. Annular dilatation is a major component in the pathology of mitral insufficiency regardless of cause. Moreover, many patients have a mitral insufficiency primarily or only due to posterior annular dilatation, since the annulus of the anterior leaflet does not dilatate because it is anchored to the fibrous skeleton of the base of the heart.

Studies of the natural history of mitral insufficiency have found that totally asymptomatic patients with severe mitral insufficiency usually progress to severe disability within five years. At present the treatment consists of either mitral valve replacements or repair, both methods requiring open heart surgery. Replacement can be performed with either mechanical or biological valves.

The mechanical valve carries the risk of thromboembolism and requires anticoagulation, with all its potential hazards, whereas biological prostheses suffer from limited durability. Another hazard with replacement is the risk of endocarditis. These risks and other valve related complications are greatly diminished with valve repair.

Mitral valve repair is theoretically possible if an essentially normal anterior leaflet is present. The basic four techniques of repair include the use of an annuloplasty ring, quadrangular segmental resection of diseased posterior leaflet, shortening of elongated chordae, and transposition of posterior leaflet chordae to the anterior leaflet.

Annuloplasty rings are needed to achieve a durable reduction of the annular dilatation. All the common rings are sutured along the posterior mitral leaflet adjacent to the mitral annulus in the left atrium. The Duran ring encircles the valve completely, whereas the others are open towards the anterior leaflet. The ring can either be rigid, like the original Carpentier ring, or flexible but non-elastic, like the Duran ring or the Cosgrove-Edwards ring.

Effective treatment of mitral insufficiency currently requires open-heart surgery, by the use of total cardiopulmonary by-pass, aortic cross-clamping and cardioplegic cardiac arrest.

To certain groups of patient, this is particular hazardous. Elderly patients, patients with a poor left ventricular function, renal disease, severe calcification of the aorta, previous cardiac surgery or other concomitant diseases, would in particular most likely benefit from a less invasive approach, even if repair is not complete. The current trend towards less invasive coronary artery surgery, without cardiopulmonary by-pass, as well as PTCA will also call for a development of a less invasive method for repair of the often concomitant mitral insufficiency.

SUMMARY OF THE INVENTION

Therefore, a first object of the present invention is to provide a device and a method for treatment of mitral insufficiency without the need for cardiopulmonary by-pass and without opening of the chest and heart.

A second object of the invention is to provide reduction of the mitral annulus using only catheter based technology.

According to the present invention, a device for treatment of mitralis insufficiency comprises an elongate body having such dimensions as to be insertable into the coronary sinus and having two states, in a first state of which the elongate body has a shape that is adaptable to the shape of the coronary sinus, and to the second state of which the elongate body is transferable from the said first state assuming a reduced radius of curvature, whereby the radius of curvature of the coronary sinus is reduced as well as the circumference of the mitral valve annulus, when the elongate body is positioned in the coronary sinus. More precisely, the elongate body comprises a distal stent section, a proximal stent section and control wires for reducing the distance between the distal and proximal stent sections.

Thus, means are provided for the transfer of the elongate body to the second state by shortening it from a larger radius of curvature to a smaller radius of curvature.

The control wires may comprise a first wire and means for guiding said first wire in a course extending two times between the distal and proximal stent sections, when the distance therebetween is at a maximum, and extending at least three times between the distal and proximal stent sections, when the distance therebetween is at a minimum.

To accomplish changes in the course, the guiding means preferably comprises a first eyelet fixed to one of the distal and proximal stent sections, a second eyelet fixed to the other of the distal and proximal stent sections, and a third eyelet positioned between the distal and proximal stent sections, said first wire having a first end fixed to said one of the distal and proximal stent section and extending therefrom via the third eyelet, the first eyelet and the second eyelet back to the third eylet where a second end of the first wire is fixed. By this structure the maximum distance between the two stent sections will be about 1.5 times the minimum distance between the two stent sections.

A larger quotient may be obtained by extending the first wire from the first eyelet at least once more via the third eyelet and the first eyelet before finally extending the first wire via the second eyelet back to the third eylet where the second end of the first wire is fixed.

In order to reduce the distance between the distal stent section and the proximal stent section, said first eyelet is preferably fixed to the distal stent section and said control wires comprise a second wire extending through the third eyelet and as a double wire proximally therefrom out of the coronary sinus and out of the human body. As an alternative to this second wire, a single wire may be used having an end releasably fixed to the third eyelet and extending as a single wire proximally therefrom out of the coronary sinus and out of the human body. However, to be able to also increase the distance between the distal stent section and the proximal stent section, said control wires may comprise a third wire extending through the third eyelet and as a double wire distally to and through the first eyelet and then as a double wire proximally therefrom out of the coronary sinus and out of the human body.

Alternatively, the distance between the distal stent section and the proximal stent section may be reduced by fixing the first eyelet to the proximal stent section. Then, said control wires should comprise a second wire extending through the third eyelet and as a double wire distally to and through the first eyelet and then as a double wire proximally therefrom out of the coronary sinus and out of the human body. In order to be able to increase the distance between the distal stent section and the proximal stent section in this case, the control wires should comprise a third wire extending through the third eyelet and as a double wire proximally therefrom out of the coronary sinus and out of the human body.

It should be noted that when the proximal and distal stent sections have been fixed relative to the coronary sinus and the distance between them thererafter has been finaly adjusted to a desired value, the second and the third wires may in both the described alternatives be withdrawn from the coronary sinus by pulling one of their ends positioned outside of the coronary sinus and outside of the human body.

In preferred embodiments of the device, a cover encloses the wires in their courses between the distal and proximal stent sections so as to eliminate the risk that the wires will injure the coronary sinus by cutting into its internal surfaces.

The cover may comprise one or more plastic sheaths and may also comprise one or more helical wires.

In an alternative embodiment, the device for treatment of mitral annulus dilatation comprises an elongate body having such dimensions as to be insertable into the coronary sinus and having two states, in a first of which the elongate body has a shape that is adaptable to the shape of the coronary sinus, and to the second of which the elongate body is transferable from said first state assuming a reduced radius of curvature, whereby the radius of curvature of the coronary sinus is reduced as well as the circumference of the mitral valve annulus, when the elongate body is positioned in the coronary sinus, said elongate body comprising at least one stent section at a distance from each end of the elongate body, said stent section providing a reduction of its length when expanded in situ in the coronary sinus, whereby the elongate body is shortened and bent to a smaller radius of curvature.

Preferably, the elongate body of this embodiment comprises a proximal stent section, a distal stent section and a central stent section, the distal and proximal stent sections being expandable prior to the central stent section. Obviously, this will result in a reduction of the distance between the proximal and distal stent sections. Further, the proximal and distal stent sections should be expandable without substantial length reduction.

Thus, the present invention takes advantage of the position of the coronary sinus being close to the mitral annulus. This makes repair possible by the use of current catheter-guided techniques.

The coronary veins drain blood from the myocardium to the right atrium. The smaller veins drain blood directly into the atrial cavity, and the larger veins accompany the major arteries and run into the coronary sinus which substantially encircles the mitral orifice and annulus. It runs in the posterior atrioventricular groove, lying in the fatty tissue between the left atrial wall and the ventricular myocardium, before draining into the right atrium between the atrial septum and the post-Eustachian sinus.

In an adult, the course of the coronary sinus may approach within 5–15 mm of the medial attachment of the posterior leaflet of the mitral valve. Preliminary measurements performed at autopsies of adults of normal weight show similar results, with a distance of 5,3±0,6 mm at the medial attachment and about 10 mm at the lateral aspect of the posterior leaflet. The circumference of the coronary sinus was 18,3±2,9 mm at its ostium (giving a sinus diameter of the septal aspect of the posterior leaflet of 5,8±0,9 mm) and 9,7±0,6 mm along the lateral aspect of the posterior leaflet (corresponding to a sinus diameter of 3,1±0,2 mm).

BRIEF DESCRIPTION OF THE DRAWINGS

The invention will be better understood by the following description of preferred embodiments referring to the appended drawings, in which.

DESCRIPTION OF THE PREFERRED EMBODIMENTS

Figure 1:
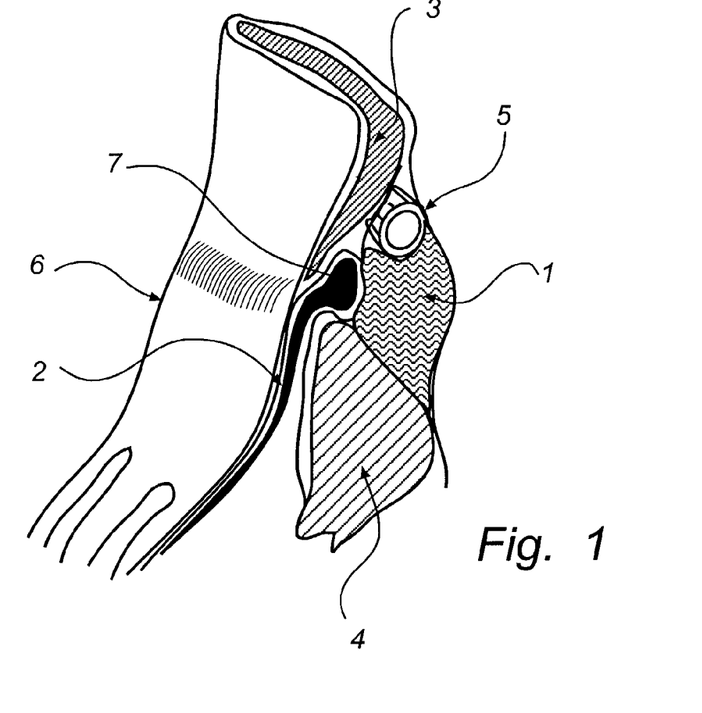
FIG. 1 is a cross-sectional view of a part of a heart.

FIG. 1 is a cross-sectional view through the heart area of the posterior atrioventricular groove 1, which is filled with fatty tissue. It shows the posterior leaflet 2 of the mitral valve and the adjoining parts 3, 4 of the atrial myocardium and the ventricular myocardium. The coronary sinus 5 is shown close to the mitral annulus 6 and behind the attachment 7 of the posterior leaflet 2. Since the coronary sinus 5 substantially encircles the mitral annulus 6, a reduction of the radius of curvature of the bent coronary sinus 5 also will result in a diameter and circumference reduction of the mitral annulus 6.

Figure 2:
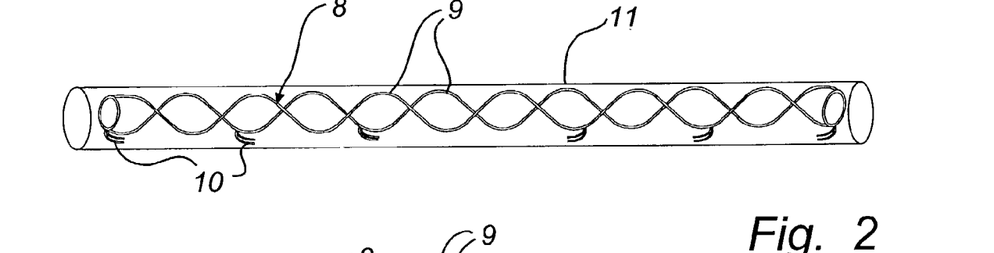
FIGS. 2 and 3 are schematic views of a first embodiment of a device according to the present invention.
Figure 3:
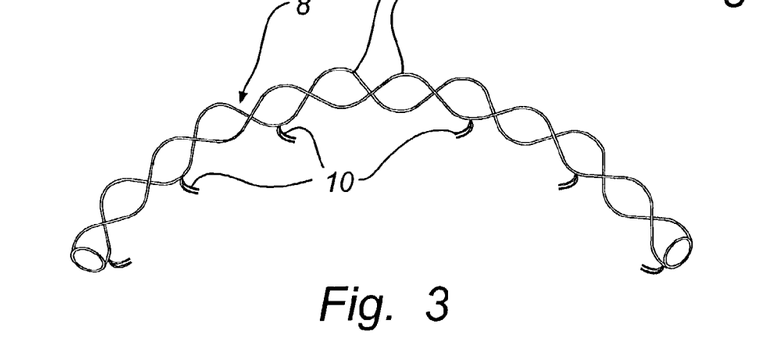

The device of FIG. 2 comprises an elongate body 8 made of memory metal, e.g. Nitinol, or other similar material which has a memory of an original shape, illustrated in FIG. 3, and can be temporary forced into another shape, illustrated in FIG. 2. This elongate body 8 comprises one, two or more memory metal strings 9 of helical or other shape so as to fit together and be able of permitting the movements described below. Along the elongate body 8 several hooks 10 are fastened so as to extend radially out therefrom. These hooks 10 are covered by a cover sheath 11 in FIG. 2.

Figure 4:
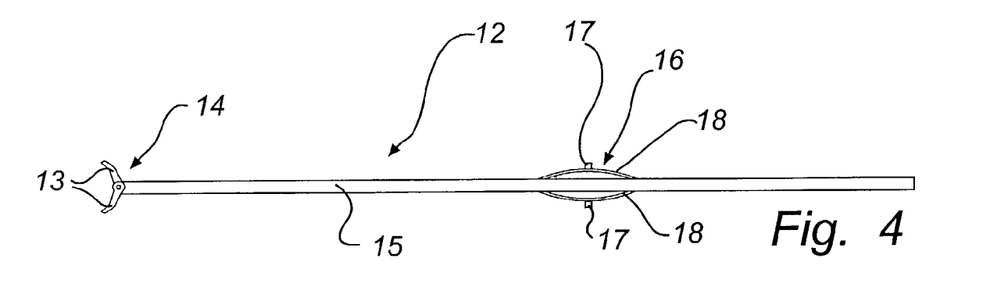
FIGS. 4–6 are schematic views illustrating an instrument, which may be used when positioning the device shown in FIGS. 2 and 3 in the coronary sinus.

The elongate body 8 is forced into a stretched or extended state by means of a stabilizing instrument 12 shown in FIG. 4. This instrument 12 has two arms 13 at a distal end 14 of a rod 15 and a locking means 16 at a proximal end of the rod 15. The distance between the ends of the rod 15 corresponds to the desired length of the elongate body 8 when being inserted into the coronary sinus 5.

Figure 5:
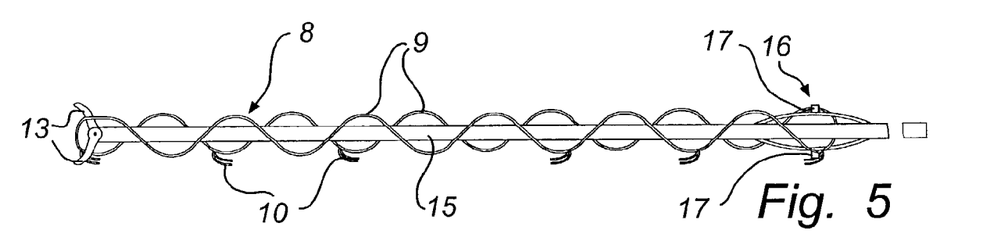
Figure 6:
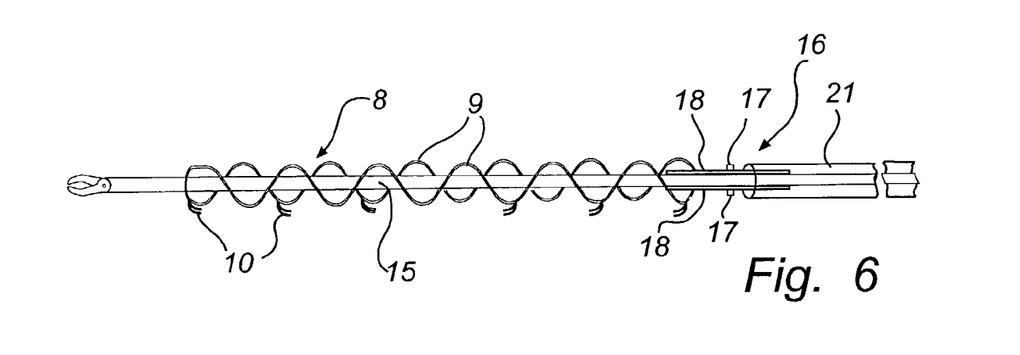

The arms 13 are free to move between the position shown in FIG. 4 and a position in alignment with the rod 15, as shown in FIG. 6. The locking means 16 has two locking knobs 17, which are pressed radially outwards from the rod 15 by two spring blades 18. Thus, the elongated body 8 can be pushed over the rod 15 of the stabilizing instrument 12, then stretched between the arms 13 and the knobs 17, and finally locked in its stretched state on the stabilizing instrument 12 between the arms 13 and the knobs 17, as illustrated in FIG. 5.

The rod 15 may be a metal wire which is relatively stiff between the distal end 14 and the locking means 16 but still so bendable that it will follow the shape of the coronary sinus 5. Proximally of the locking means 16 the metal wire of the stabilizing instrument 11 is more pliable to be able to easily follow the bends of the veins.

The above-described elongate body 8 is positioned in the coronary sinus 5 in the following way:

An introduction sheath (not shown) of synthetic material may be used to get access to the venous system. Having reached access to the venous system, a long guiding wire (not shown) of metal is advanced through the introduction sheath and via the venous system to the coronary sinus 5. This guiding wire is provided with X-ray distance markers so that the position of the guiding wire in the coronary sinus 5 may be monitored.

Figure 8:
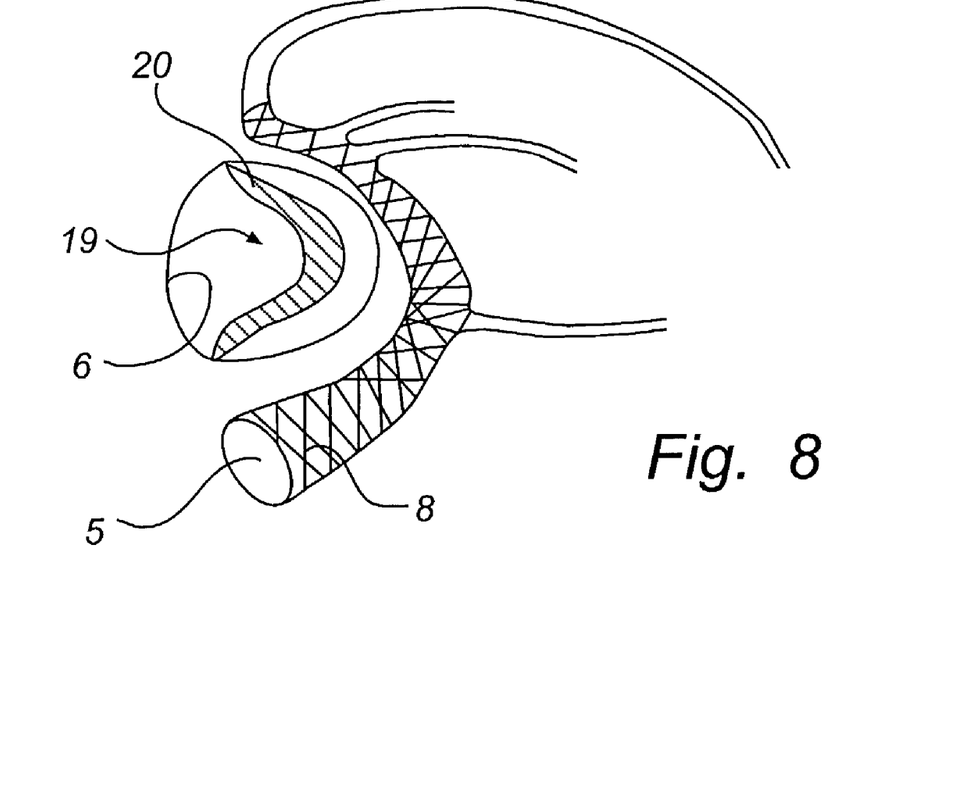
FIGS. 8 and 9 are schematic views illustrating the positioning of the device of FIGS. 2 and 3 in the coronary sinus.

The elongate body 8 is locked onto the stabilizing instrument 12, as shown in FIG. 5, and introduced into the long cover sheath 11 of synthetic material. This aggregate is then pushed through the introduction sheath and the venous system to the coronary sinus 5 riding on the guiding wire. After exact positioning of the elongate body 8 in the coronary sinus 5, as illustrated in FIG. 8 where the mitral valve 19 is shown having a central gap 20, the cover sheath 11 is retracted exposing the elongate body 8 within the coronary sinus 5. This maneuver allows the hooks 10 on the elongate body 8 to dig into the walls of the coronary sinus 5 and into the heart. The elongate body 8 is still locked on to the stabilizing instrument 12 such that the hooks 10 engage the walls of the coronary sinus 5 in the stretched or extended state of the elongate body 8.

Figure 9:
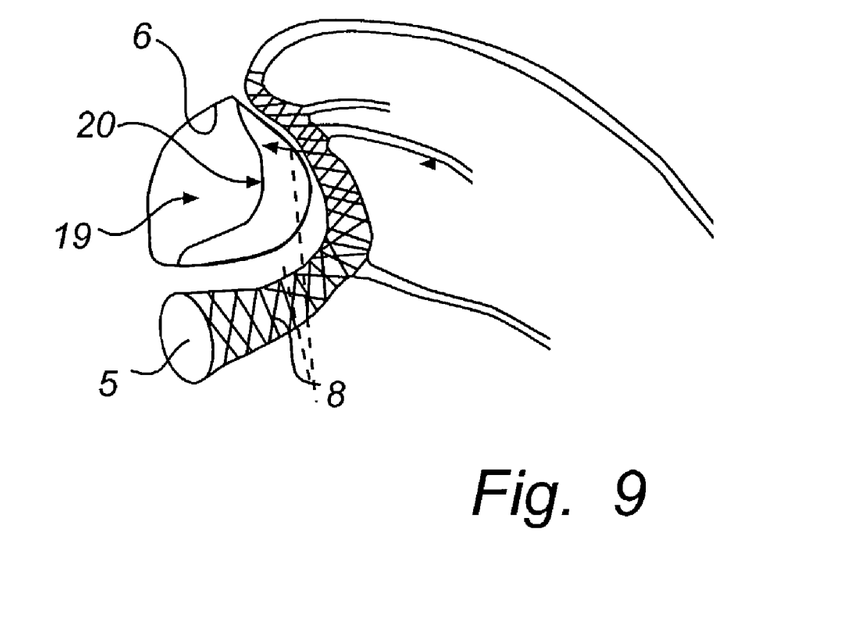

A catheter 21, shown in FIG. 6, is pushed forward on the guiding wire and the rod 15 for releasing the elongate body 8 from the locking means 16 by pressing the spring blades 18 towards the rod 15. This movement releases the knobs 17 as well as the arms 13 from engagement with the elongate body 8 which contracts as illustrated in FIG. 9, thereby shortening the radius of curvature of the coronary sinus. As a result, the mitral valve annulus 6 shrinks moving the posterior part thereof forward (shown by arrows in FIG. 9). This movement reduces the circumference of the mitral valve annulus 6 and thereby closes the central gap 20.

Figure 7:
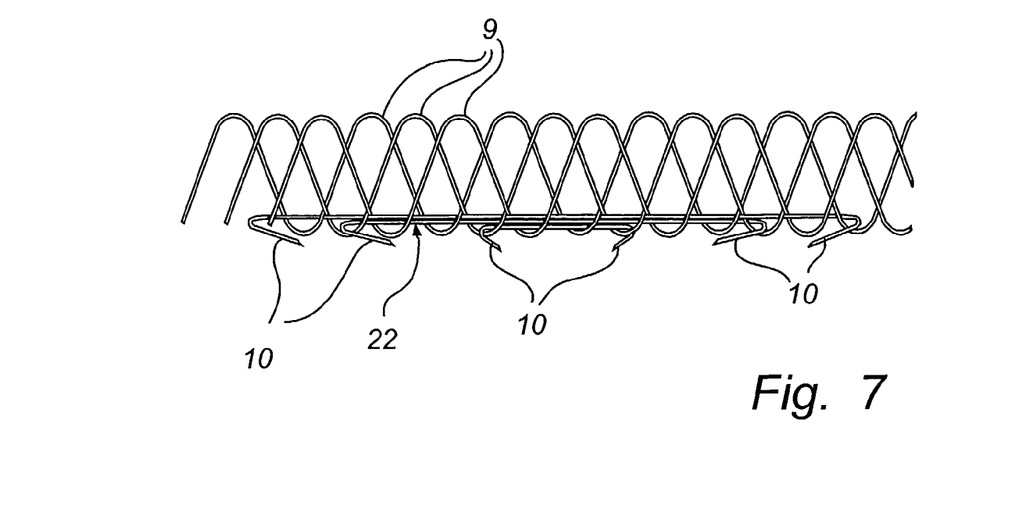
FIG. 7 is a partial, enlarged view of the first embodiment shown in FIG. 2.

FIG. 7 illustrates a part of an arrangement of the wires 9 and the hooks 10 along a peripheral part of the elongate body 8, whereby the elongate body 8 will be asymmetrically contracted resulting in a bending thereof when interconnecting parts 22 of at least some of the hooks 10 are shortened to an original shape.

Figure 10:
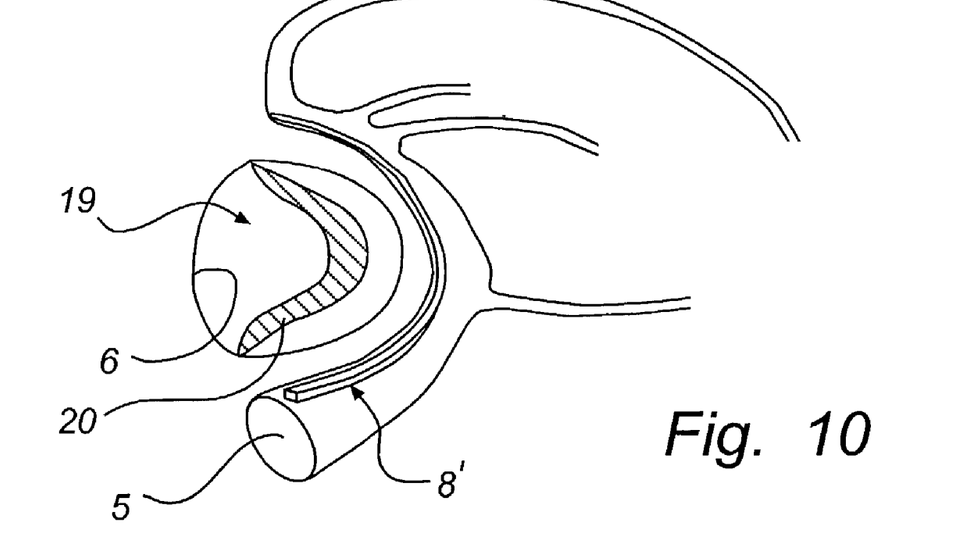
FIGS. 10 and 11 are schematic views illustrating the positioning of a second embodiment of the device according to the present invention in the coronary sinus.
Figure 11:
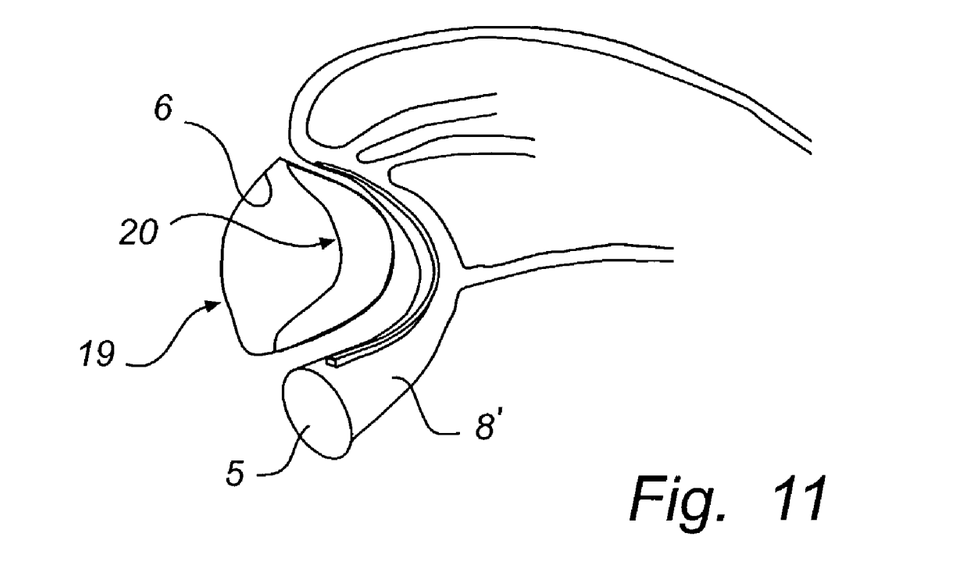

FIGS. 10 and 11 illustrate an alternative embodiment of an elongate body 8', which is a solid wire in the shape of an open U-shaped ring that will engage the wall of the coronary sinus 5 most adjacent to the mitral valve annulus 6 when inserted into the coronary sinus 5. The elongate body 8' consists of a memory metal material which when reverting to its original shape will bend as illustrated in FIG. 11. The return of the open ring 8' to its original shape may be initiated in several ways, as is obvious to the man skilled in the art.

Figure 12:
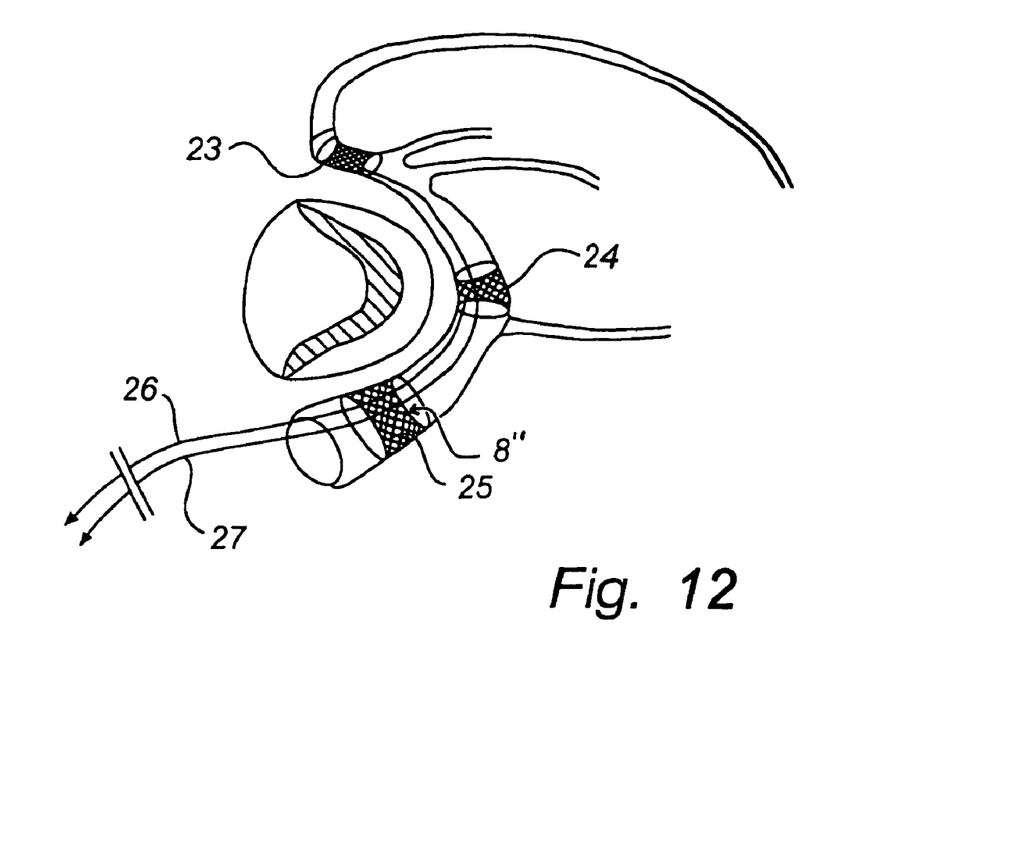
FIGS. 12 and 13 are schematic views illustrating the positioning of a third embodiment of the device according to the present invention in the coronary sinus.
Figure 13:
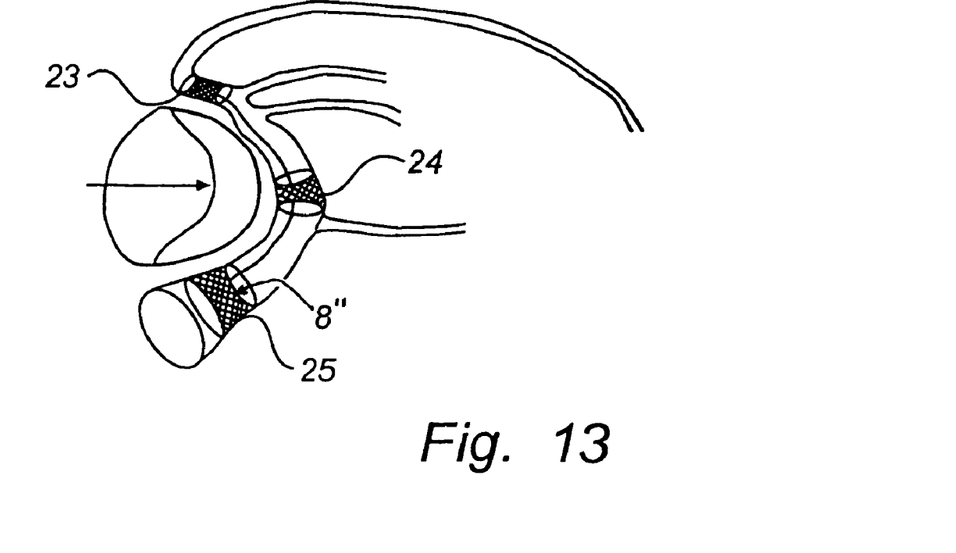

The third embodiment of the elongate body 8", illustrated in FIGS. 12 and 13, comprises three stent sections 23–25 positioned at one end of the elongate body 8", at the middle thereof and at the other end of the elongate body 8", respectively. These stent sections 23–25 may be positioned in the coronary sinus 5 as illustrated by conventional means, such that their positions are fixed. They are connected by wires 26, 27, which may be maneuvered from outside the vein system such that the distances between the adjacent stent sections 23, 24 and 24, 25 are reduced. More specifically, these distances are reduced asymmetrically, i.e. more on the side of coronary sinus 5 most adjacent to the posterior part of the mitral valve annulus 6. Thereby, the elongate body 8" is bent, as illustrated in FIG. 13, and presses the coronary sinus 5 against the mitral valve annulus 6 closing the gap 20.

Figure 14:
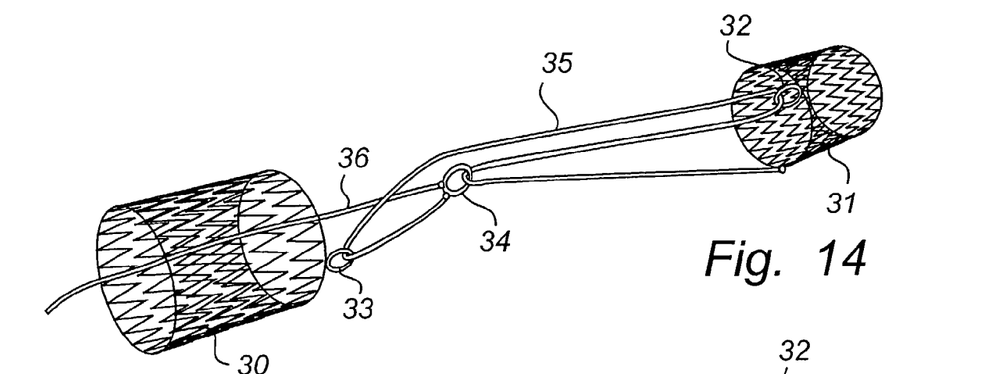
FIG. 14 illustrates a fourth embodiment of the device according to the present invention.

A fourth embodiment of the device is shown in FIG. 14 as comprising two stent sections, more precisely a proximal stent section 30 and a distal stent section 31. The fourth embodiment further comprises a first eyelet 32, which is fixed to a preferably proximal part of the the distal stent section 31, a second eyelet 33, which is fixed to a preferably distal part of the proximal stent section 30, and a third eyelet 34, which is positioned between the proximal and distal stent sections 30, 31. These sections 30, 31 are joined by a wire 35, one end of which is fixed to the the distal stent section 31. The wire 35 may be fixed to the distal stent section 31 at a proximal point, as shown in FIG. 14, or at a more distal point up to the distal end of the distal stent section 31.

From the distal stent section 31 the wire 35 extends to and through the third eyelet 34 and then back towards the distal stent section 31 to and through the first eyelet 32. From the first eyelet 32 the wire 35 then extends to and through the second eyelet 33 and then finally to the third eyelet 34, the other end of the wire 35 being fixed to this third eyelet 34.

By moving the third eyelet 34 towards the proximal stent section 30, the distance between the proximal and distal stent sections 30, 31 will be reduced. On the contrary, by moving the third eyelet 34 towards the distal stent section 31, the distance between the proximal and distal stent sections may be increased. However, such increase will require some means pushing the distal stent section 31 in a distal direction away from the proximal stent section 30 or pulling the proximal stent section in a proximal direction away from the distal stent section 31.

The distance between the proximal and distal stent sections 30, 31 will reach a maximum when the third eyelet 34 is positioned close to the distal stent section 31 and will reach a minimum when the third eyelet 34 is positioned close to the proximal stent section 30.

The third eyelet 34 may be moved towards the proximal stent section 30 by means of a single wire 36, which has an end releasably fixed to the third eyelet 34 and extends proximally therefrom through the proximal stent section 30 and furter proximally out of the coronary sinus 5, through the vein system and out of the human body.

Figures 15, 16, 17:
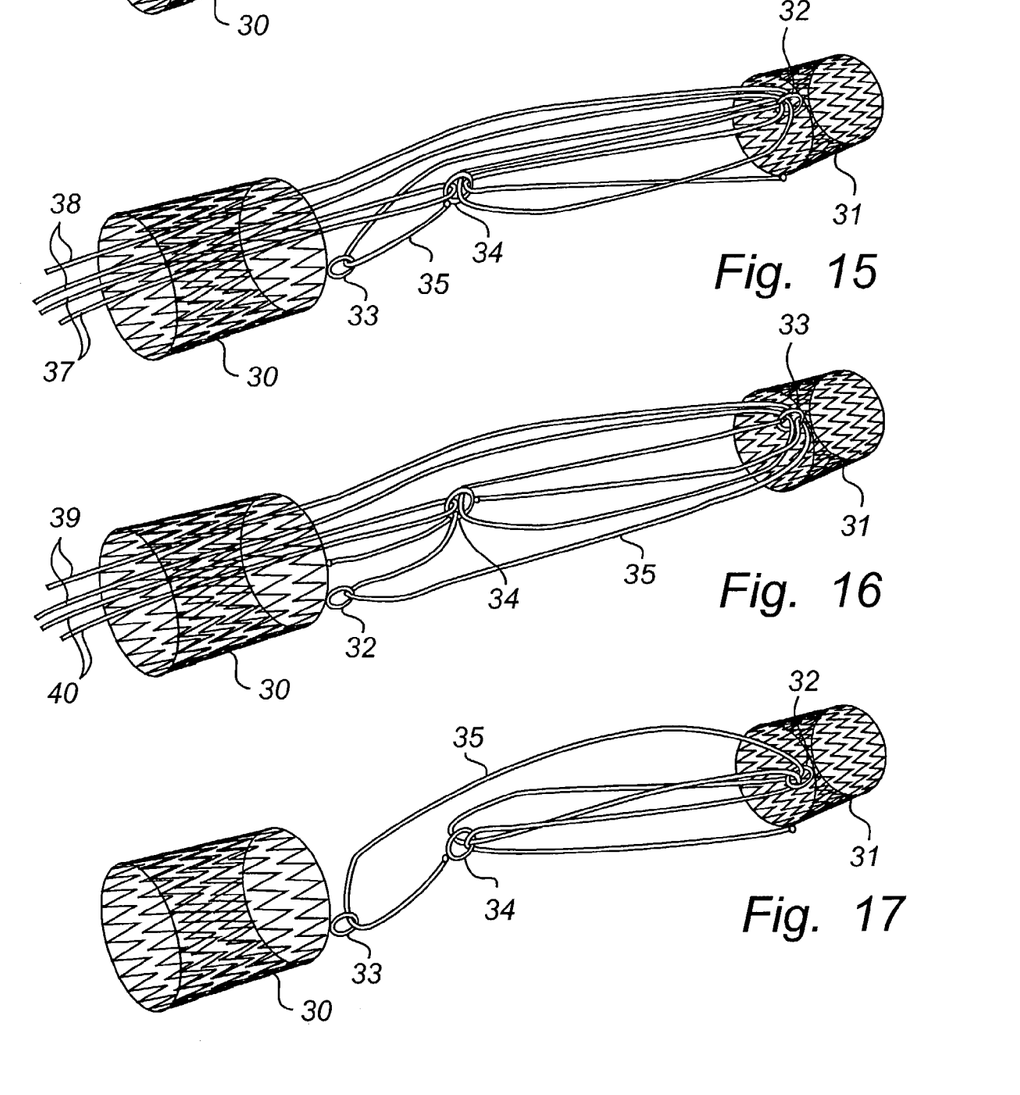
FIG. 15 is a schematic view illustrating a preferred operation of the fourth embodiment.
FIG. 16 is a schematic view illustrating the operation of a fifth embodiment of the device according to the present invention.
FIG. 17 illustrates a sixth embodiment of the device according to the present invention.

In a preferred embodiment schematically illustrated in FIG. 15, a second wire 37 extends through the third eyelet 34 and further extends as a double wire proximally from the third eyelet 34, through the proximal stent section 30 and the coronary sinus 5 and then out of the body. The third eyelet 34 will be moved proximally by simultaneous pulling both ends of the second wire 37 outside of the body. When the desired position of the third eyelet 34 is reached, the second wire 37 may easily be removed through the vein system by pulling only one of its ends outside the body.

As illustrated in FIG. 15, a third wire 38 may be extended through the third eyelet 34. Therefrom it extends as a double wire distally to and through the first eyelet 32 and then this double wire extends proximally from the first eyelet 32 (or a further eyelet fixed to the proximal end of the distal stent) through the proximal stent section 30 and finally the double wire 38 extends proximally through the coronary sinus 5 and out of the human body. By pulling both ends of this third wire 38 outside of the body, the third eyelet 34 will allow a movement of the proximal and distal stent sections 30, 31 away from each other. By means of the second wire 37 and the third wire 38 the position of the third eyelet 34 may be adjusted repeatedly until a desired position is attained. The third wire 38 may be removed in the same manner as the second wire 37.

Obviously, the position of the third eyelet 34 may be used to control the distance between the proximal and distal stent sections 30, 31, and this distance controls the radius of curvature of the device and thus also the radius of curvature of the coronary sinus 5.

The furter embodiment of the device illustrated in FIG. 16 corresponds to the embodiment illustrated in FIG. 15 except that the first eyelet 32 is fixed to the proximal stent section 30 and the second eyelet 33 is fixed to the distal stent section 31. Therefore, a fourth wire 39 has the same extension as the third wire 38 in FIG. 15 but has the function of the second wire 37 in FIG. 15. A fifth wire 40 has the same extension as the second wire 37 in FIG. 15 but has the function of the third wire 38 of FIG. 15.

The quotient between the maximum distance and the minimum distance between the proximal stent section 30 and the distal stent section 31 in FIGS. 15 and 16 is about 1.5. A quotient of about 2.5 would be possible by letting the wire 35 extend once more via the third eyelet 34 and the first eyelet 32 (or another eyelet fixed at substantially the same position as the first eyelet) before finally extending via the second eyelet 33 back to the third eyelet 34 where the second end of the wire 35 is fixed, as shown in FIG. 17.

Figure 18:
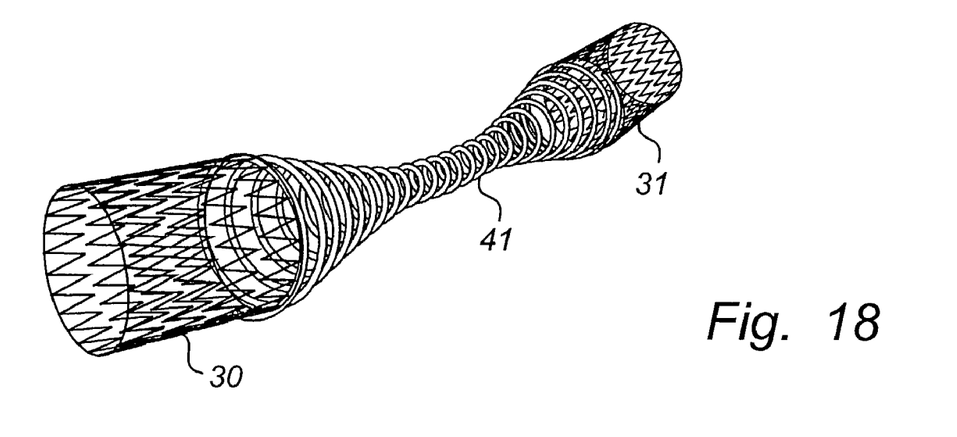
FIG. 18 illustrates a further modification of the embodiments of FIGS. 14–17.

According to FIG. 18, the wires 35–40 extending between the proximal stent section 30 and the distal stent section 31 are confined in a plastic sheath or a plastic wire spiral 41 which will cover and protect the wires 35–40. By enclosing the wires 35–40, the sheath or spiral 41 will also prohibit them from cutting through the wall of the coronary sinus 5. Alternatively, more than one sheath or spiral 41 may be used, all of which should be compressible lengthwise so as to allow the reduction of the distance between the proximal and distal stent sections 30, 31.

The embodiments illustrated in FIGS. 15–18 may be introduced by conventional means into the coronary sinus 5 via the vein system. Preferably, the distal stent section 31 first is adjusted to a desired position, whereupon it is expanded so as to engage the walls of the coronary sinus 5. Thereby, the position of the distal stent section 31 is fixed in the coronary sinus 5. Then the position of the proximal stent section 30 is adjusted considering the required reduction of the distance between the the proximal and distal stent sections 30, 31. Thereafter the proximal stent section 30 is expanded such that it is fixed relative the coranary sinus 5. Finally, the distance between the proximal and distal stent sections 30, 31 is reduced using one of the wires 37 and 39. If the distance reduction is found too extensive, the distance between the stent sections 30 and 31 may be increased by pulling one of the wires 38 and 40. After achieving a perfect position, the used wires 37–40 may be removed by pulling in one of the double ends.

It should be noted that instead of eyelets having a single opening, eyelets having multiple openings could be used such that each one of the wires extends through an opening of its own.

Figure 19:
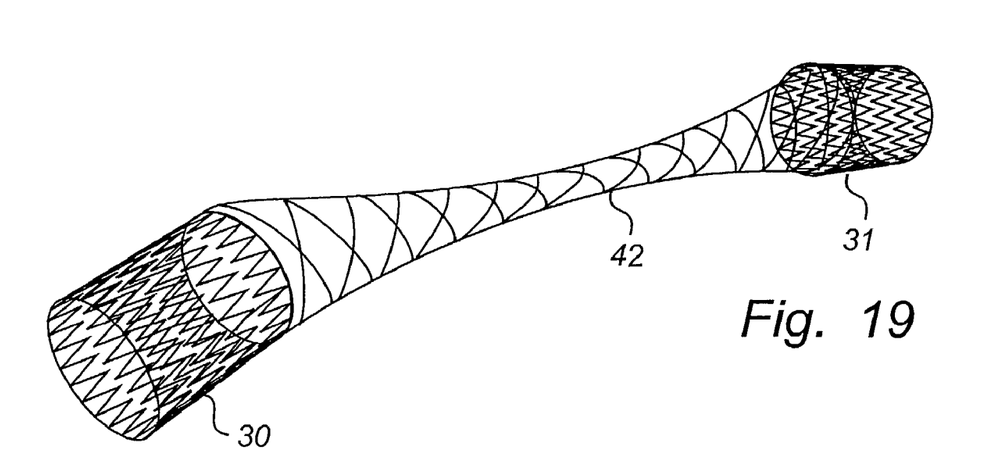
FIGS. 19 and 20 illustrate a seventh embodiment of the device according to the present invention.
Figure 20:
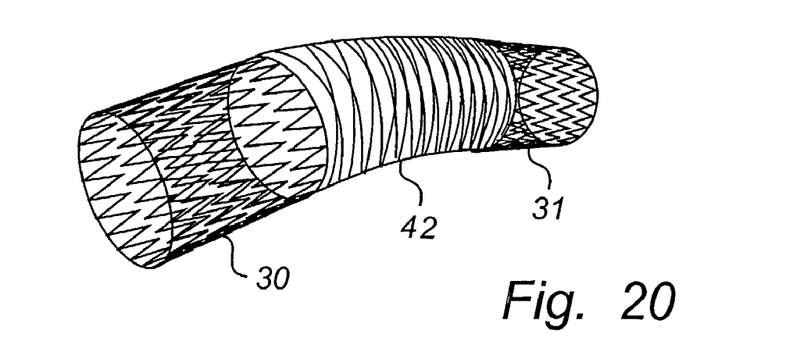

Still one further embodiment of the device according to the present invention is illustrated in FIGS. 19 and 20. Here, the device comprises an elongate body having three stent sections, the proximal stent section 30 and the distal stent section 31 being of the same type as described above. A central stent section 42 is such as to reduce its length when expanded radially.

When this device is positioned in the coronary sinus 5, the proximal and distal sections 30, 31 are first expanded, as illustrated in FIG. 19, and then the central stent section 42 is expanded. As a consequence of its length reduction when expanded, the central stent section 42 will reduce the distance between the proximal and distal stent sections 30, 31 and thus reduce the radius of curvature of the coronary sinus 5, as illustrated in FIG. 20.

Concludingly, the present invention provides a device placed in the coronary sinus 5 and designed to reduce the dilatation of the mitral annulus. This device is at a distance from the attachment of the posterior leaflet that does not much exceed the distance at which present annuloplasty rings are placed by open surgery techniques, and the coronary sinus is along its entire course large enough to hold such a device. The device could be positioned by catheter technique or any other adequate technique and offers a safer alternative to the current open surgery methods. The device could be designed or heparincoated so as to avoid thrombosis in the coronary sinus, thus reducing the need for aspirin, ticlopedine or anticoagulant therapy.

It is to be understood that modifications of the above-described device and method can be made by people skilled in the art without departing from the spirit and scope of the invention.

What is claimed is:

1. A device for treating mitral valve dilatation configured to be placed in the coronary sinus of a heart adjacent to the mitral valve annulus, the device comprising an elongate body made at least in part of a memory metal, wherein the elongate body is configured to asymmetrically contract after placement in the coronary sinus such that the elongate body applies a force along a portion of the atrial wall of the coronary sinus adjacent to the mitral valve annulus to press the coronary sinus against a portion of the mitral valve annulus.

2. The device of claim 1 wherein at least a portion of the elongate body comprises an expandable structure that expands from a collapsed condition to an expanded condition for engagement with the walls of the coronary sinus.

3. The device of claim 2 wherein the expandable structure is a stent section.

4. The device of claim 2 wherein the expandable structure is cylindrical in configuration.

5. The device of claim 1 wherein the elongate body applies the force to a plurality of portions of the atrial wall of the coronary sinus.

6. The device of claim 1, wherein the elongate body further comprises a proximal stent section and a distal stern section and wherein the proximal and distal stent sections are expandable for engagement with the walls of the coronary sinus.

7. The device of claim 6, wherein the proximal and distal stent sections are joined by a wire.

8. The device of claim 7, further comprising a first eyelet fixed to the proximal stent section and a second eyelet fixed to the distal stent section, wherein the wire extends through the first and second eyelets.

9. A method of treating dilatation of a mitral valve annulus including delivering a mitral valve therapy device through a venous system to a coronary sinus and deploying the device such that a distal end of the device is spaced distally from a proximal end of the device, wherein the device applies a force to a portion of an atrial wall of a coronary sinus to press the coronary sinus against a portion of the mitral valve annulus to change the shape of the mitral valve annulus.

10. The method of claim 9 wherein the deploying step comprises retracting a cover sheet to expose the device in the coronary sinus, the device being formed of a memory material and configured for applying the force to press the coronary sinus against the mitral valve annulus.

11. The method of claim 9 wherein the device is expandable from a collapsed condition to a deployed condition, wherein the delivering step is carried out while the device is in the collapsed condition, and wherein the deploying step further includes expanding the device after the device is delivered at least partially into the coronary sinus.

12. The method of claim 9 wherein the force is applied to a plurality of portions of the atrial wall of the coronary sinus.

13. The method of claim 12 wherein the mitral valve therapy device comprises an elongate body made at least in part of a memory material and sized for insertion into the coronary sinus, the elongate body being configured for applying the force to the plurality of portions of the coronary sinus.

14. The method of claim 13 wherein at least a portion of the elongate body is expandable from a collapsed condition to a deployed condition, wherein the delivering step is carried out while the device is in the collapsed condition, and wherein the deploying step further includes expanding the device after the device is delivered into the coronary sinus.

* * * * *